(12) United States Patent
Heyer et al.

(10) Patent No.: US 6,515,203 B1
(45) Date of Patent: Feb. 4, 2003

(54) NUCLEIC ACID MOLECULES ENCODING ENZYMES HAVING FRUCTOSYL POLYMERASE ACTIVITY

(75) Inventors: Arnd G. Heyer, Berlin (DE); Elke Hellwege, Berlin (DE); Dominique Gritscher, Berlin (DE)

(73) Assignee: Max-Planck-Gesellschaft zur Forderung der Wissenschaften E.V., Berlin (DE)

( * ) Notice: Subject to any disclaimer, the term of this patent is extended or adjusted under 35 U.S.C. 154(b) by 0 days.

(21) Appl. No.: 09/390,224

(22) Filed: Sep. 3, 1999

Related U.S. Application Data

(63) Continuation of application No. PCT/EP98/01156, filed on Mar. 2, 1998.

(30) Foreign Application Priority Data

Mar. 4, 1997 (DE) ......................................... 197 08 774

(51) Int. Cl.[7] .................... C12N 15/29; C12N 15/82; C12N 15/54; A01H 5/00; C12P 19/04
(52) U.S. Cl. .................... 800/284; 800/278; 800/287; 800/317.2; 800/320; 800/320.1; 800/320.2; 800/320.3; 435/69.1; 435/101; 435/193; 435/320.1; 435/419; 435/468; 536/23.6
(58) Field of Search .................... 536/23.6; 435/69.1, 435/320.1, 419, 468, 101, 193; 800/278, 284, 287, 317.2, 320, 320.2, 320.3, 320.1

(56) References Cited

FOREIGN PATENT DOCUMENTS

| WO | WO 94/14970 | 7/1994 |
|---|---|---|
| WO | WO 95/13389 | 5/1995 |
| WO | WO 96/01904 | 1/1996 |
| WO | WO 96/21023 | 7/1996 |
| WO | WO 97/29186 | 8/1997 |

OTHER PUBLICATIONS

Hellwege et al. Accession No. Y09662, Nov. 1996.*

Elke M. Hellwege, et al., "Differences in Chain Length Distribution of Inulin from *Cynara scolymus* and *Helianthus tuberosus* are Reflected in a Transient Plant Expression System Using the Respective 1– FFT cDNAs," *FEBS Letters*, 427, pp. 25–28 (1998).

Elke M. Hellwege et al., "Transgenic Potato Tubers Accumulate High Levels of 1–Kestose and Nystose: Functional Identification of a Sucrose 1–Fructosyltransferase of Artichoke (*Cynara scolymus*) Blossom Discs," *The Plant Journal*, 12(5), pp. 1057–1065 (1997).

Norbert Sprenger et al., "Fructan Synthesis in Transgenic Tobacco and Chicory Plants Expressing Bartley Sucrose: Fructan 6–Fructosyltransferase," *FEBS Letters*, 400, pp. 355–358 (1997).

I. Vijn et al., "Fructan of the Inulin Neoseries is Synthesized in Transgenic Chicory Plants (*Cichorium intybus* L.) Harbouring Onion (*Allium cepa* L.) Fructan:Fructan 6G–Fructosyltransferase," *The Plant Journal*, 11(3), pp. 387–398 (1997).

\* cited by examiner

Primary Examiner—David T. Fox
(74) Attorney, Agent, or Firm—Fish & Neave; James F. Haley, Jr.; Karen E. Brown

(57) ABSTRACT

Described are nucleic acid molecules encoding enzymes having fructosyl polymerase activity. These enzymes are sucrose dependent sucrose fructosyltransferases (SST) enzymes. Furthermore, vectors and host cells are described containing the nucleic acid molecules, in particular transformed plant cells and plants that can be regenerated from them and that express the described SSTs. Furthermore, methods for the production of short-chain fructosyl polymers using the described hosts and/or the SSTs produced by them are described.

20 Claims, 4 Drawing Sheets

NUCLEIC ACID MOLECULES ENCODING ENZYMES HAVING FRUCTOSYL POLYMERASE ACTIVITY

CROSS-REFERENCE TO A RELATED APPLICATION

This application is a continuation of copending international application PCT/EP98/01156, filed Mar. 2, 1998, which designated the United States and which is incorporated by reference herein.

FIELD OF THE INVENTION

The present invention relates to nucleic acid molecules encoding sucrose dependent sucrose fructosyltransferases (SST). Furthermore, this invention relates to vectors and hosts containing such nucleic acid molecules, as well as plant cells and plants transformed with the described nucleic acid molecules. Furthermore, methods for the production of transgenic plants are described that synthesize short-chain fructosyl polymers due to the introduction of DNA molecules encoding an SST from artichoke. The present invention also relates to methods for the production of SST for producing short-chain fructosyl polymers in various host organisms as well as to the SST with the help of which short-chain fructosyl polymers can be produced using various methods, for example fermentative or other biotechnological methods.

Water-soluble, linear polymers have many various applications, for example for increasing the viscosity of aqueous systems, as detergents, as suspending agents or for accelerating the sedimentation process and for complexing but also for binding water. Polymers on the basis of saccharides, for example fructosyl polysaccharides, are especially interesting raw materials since they are biodegradable. Apart from their application as regenerative raw materials for industrial production and processing, fructosyl polymers are also interesting as food additives, for example as artificial sweeteners. Polymers having a low polymerization level are particularly suitable for this purpose.

Up to now only processes for the production of long-chain fructane polysaccharides in plants by expression of enzymes of bacterial origin as well as a process for the production of transgenic plants expressing fructosyltransferases from *Helianthus tuberosus* have been described. Processes for the production of enzymes for producing short-chain fructosyl polymers are not known. In the specification of PCT/USA89/02729 the possibility to produce carbohydrate polymers, in particular dextrane or polyfructose, in transgenic plants, in particular in the fruits of transgenic plants, is described. For the production of such modified plants the use of levan sucrases from microorganisms, in particular from *Aerobacter levanicum, Streptococcus salivarius* and *Bacillus subtilis*, or from dextran sucrases from *Leuconostoc mesenteroides* are suggested. The production of neither the active enzymes nor of levan or dextrane nor of transgenic plants is described. The specification of PCT/EP93/02110 discloses a process for the production of transgenic plants expressing the lsc gene of levan sucrase from the gram-negative bacterium *Erwinia amylovora*. In the specification of PCT/NL93/00279 the transformation of plants having chimeric genes that contain the sacB gene from *Bacillus subtilis* or the ftf gene from *Streptococcus mutans* is described. In the case of the sacB gene a modification in the 5'-untranslated region of the gene is recommended in order to increase the expression level in transgenic plants. The specification of PCT/NL96/00012 discloses DNA sequences encoding the enzymes synthesizing carbohydrate polymers and the production of transgenic plants with the help of these DNA sequences. The disclosed sequences originate from *Helianthus tuberosus*. According to PCTL/NL96/00012 the disclosed sequences are not only suitable to modify the fructane profile of, for example, petunia and potato but also of *Helianthus tuberosus* itself. Therefore, the specification of PCT/NL96/100012 describes inter alia transgenic potato plants expressing an SST from *Helianthus tuberosus*. Even though the enzymatic activity of the SST expressed in the transgenic plants could be detected, only a low level of conversion of the substrate sucrose to short-chain fructosyl polymers could be achieved. This may be related to various factors, such as a low affinity of the enzyme to its substrate or a possible inhibition of the enzyme by the produced product.

SUMMARY OF THE INVENTION

Therefore, the problem of the present invention is to provide nucleic acid molecules encoding a sucrose dependent sucrose fructosyltransferase (SST) with the help of which it is possible to produce organisms modified by genetic engineering that are able to form short-chain fructosyl polymers.

This problem is solved by providing the embodiments described in the claims.

Therefore, the present invention relates to nucleic acid molecules encoding the proteins having the biological activity of an SST and being selected from the group consisting of (a) nucleic acid molecules encoding a protein that comprises the amino acid sequence depicted in SEQ ID No. 2 and SEQ ID No. 4;

(b) nucleic acid molecules comprising the nucleotide sequence depicted in SEQ ID No. 1 or a corresponding ribonucleotide sequence;

(c) nucleic acid molecules comprising the nucleotide sequence depicted in SEQ ID No. 3 or a corresponding ribonucleotide sequence;

(d) nucleic acid molecules hybridizing to the nucleic acid molecules mentioned in (a) or (b) and encoding an SST the amino acid of which is to at least 90% identical to the amino acid sequence depicted in SEQ ID No. 2; and (e) nucleic acid molecules the nucleotide sequence of which deviates from the sequence mentioned in (a), (b) or (c) due to the degeneration of the genetic code.

In the context of the present invention an enzyme having the fructosyl polymerase activity is understood to be a protein that is able to catalyze the linking of β-2,1 glycosidic or β-2,6 glycosidic bonds between fructose units. Hereby, a fructosyl residue to be transferred can originate from sucrose or a fructan polymer.

A short-chain fructosyl polymer is understood to be a molecule containing at least two but not more than 100 fructosyl residues that are linked either β-2,1 glycosidically or β-2,6 glycosidically. The fructosyl polymer can carry a glucose residue at its terminal that is linked via the C-1 OH-group of the glucose and the C-2 OH-group of a fructosyl. In this case a molecule of sucrose is contained in the fructosyl polymer.

In a preferred embodiment the nucleic acid sequences of the invention are derived from artichoke.

It was surprisingly found that during the expression of the nucleic acid molecules of the invention large amounts of fructosyl polymers were produced.

In contrast to the potatoes described in the specification of PCT/NL96/00012 a large amount of oligofructan is obtained that is even larger than the cellular content of the substrate sucrose when the nucleic acid molecules of the invention are used.

The nucleic acid molecules of the invention can be both DNA and RNA molecules. Suitable DNA molecules are, for example, genomic or cDNA molecules. The nucleic acid molecules of the invention can be isolated from natural sources, preferably artichoke, or can be synthesized according to known methods.

By means of conventional molecular biological processes it is possible (see, e.g., Sambrook et al., 1989, Molecular Cloning, A Laboratory Manual, $2^{nd}$ edition Cold Spring Harbor Laboratory Press, Cold Spring Harbor, N.Y.) to introduce different mutations into the nucleic acid molecules of the invention. As a result proteins with possibly modified biological properties are synthesized. One possibility is the production of deletion mutants in which nucleic acid molecules are produced by continuous deletions from the 5'- or 3'-terminal of the coding DNA sequence and that lead to the synthesis of proteins that are shortened accordingly. By such deletions at the 5'-terminal of the nucleotide sequence it is, for example, possible to identify amino acid sequences that are responsible for the translocation of the enzyme in the plastids (transition peptides). This allows the specific production of enzymes that are, due to the removal of the corresponding sequences, no longer located in the vacuole but in the cytosol or that are, due to the addition of other signal sequences, located in other compartments.

Another possibility is the introduction of single-point mutation at positions where a modification of the amino acid sequence influences, e.g., the enzyme activity or the regulation of the enzyme. By this method mutants can be produced, for example, that possess a modified $K_m$-value or that are no longer subject to the regulation mechanisms that normally exist in the cell with regard to allosteric regulation or covalent modification.

Furthermore, mutants can be produced showing a modified substrate or product specificity. Also mutants can be produced showing a modified activity-temperature profile.

For the manipulation in prokaryotic cells by means of genetic engineering the nucleic acid molecules of the invention or parts of these molecules can be introduced into plasmids allowing a mutagenesis or a modification of a sequence by recombination of DNA sequences. By means of conventional methods (cf. Sambrook et al., 1989, Molecular Cloning: A Laboratory Manual, $2^{nd}$ edition, Cold Spring Harbor Laboratory Press, N.Y., USA) bases can be exchanged and natural or synthetic sequences can be added. In order to link the DNA fragments with each other adapters or linkers can be added to the fragments. Furthermore, manipulations can be performed that provide suitable cleavage sites or that remove superfluous DNA or cleavage sites. If insertions, deletions or substitutions are possible, in vitro mutagenesis, primer repair, restriction or ligation can be performed. As analysis method usually sequence analysis, restriction analysis and other biochemical or molecular biological methods are used.

The term "hybridization" in the context of this invention has the meaning of hybridization under conventional hybridization conditions, preferably under stringent conditions as described, for example, in Sambrook et al., Molecular Cloning, A Laboratory Manual, $2^{nd}$ edition (1989) Cold Spring Harbor Laboratory Press, Cold Spring Harbor, N.Y.

Nucleic acid molecules that hybridize to the molecules of the invention can be isolated, e.g., from genomic or cDNA libraries that were produced from artichoke. In order to identify and isolate such nucleic acid molecules the molecules of the invention or parts of these molecules or the reverse complements of these molecules can be used, for example by means of hybridization according to conventional methods (see, e.g., Sambrook et al., 1989, Molecular Cloning, A Laboratory Manual, $2^{nd}$ edition Cold Spring Harbor Laboratory Press, Cold Spring Harbor, N.Y.). As a hybridization probe nucleic acid molecules can be used, for example, that have exactly or basically the nucleotide sequence depicted in Seq ID No. 1 or parts of these sequences. The fragments used as hybridization probe can be synthetic fragments that were produced by means of conventional synthesis methods and the sequence of which basically corresponds to the sequence of a nucleic acid molecule of the invention.

The molecules hybridizing to the nucleic acid molecules of the invention also comprise fragments, derivatives and allelic variants of the nucleic acid molecules described above encoding a protein of the invention. "Fragments" are understood to be parts of the nucleic acid molecules that are long enough to encode one of the described proteins. The term "derivative" in this context means that the sequences of these molecules differ from the sequences of the nucleic acid molecules described above at one or several positions but have a high level of homology to these sequences. Homology hereby means a sequence identity of at least 40%, in particular an identity of at least 60%, preferably of more than 80% and particularly preferred of more than 90%. These proteins encoded by the nucleic acid molecules have a sequence identity to the amino acid sequence depicted in SEQ ID No. 2 of at least 80%, preferably of 85% and particularly preferred of more than 90%, 95%, 97% and 99%. The deviations to the above-described nucleic acid molecules may have been produced by deletion, substitution, insertion or recombination.

The nucleic acid molecules that are homologous to the above-described molecules and that represent derivatives of these molecules usually are variations of these molecules that represent modifications having the same biological function. They can be naturally occurring variations, for example sequences from other organisms, or mutations that can either occur naturally or that have been introduced by specific mutagenesis. Furthermore, the variations can be synthetically produced sequences. The allelic variants can be either naturally occurring variants or synthetically produced variants or variants produced by recombinant DNA processes.

The proteins encoded by the various variants of the nucleic acid molecules of the invention show certain common characteristics, such as enzyme activity, molecular weight, immunological reactivity or conformation or physical properties like the electorphoretical mobility, chromatographic behavior, sedimentation coefficients, solubility, spectroscopic properties, stability; pH optimum, temperature optimum.

In another preferred embodiment the invention relates to nucleic acid molecules specifically hybridizing to transcripts of the nucleic acid molecules. These nucleic acid molecules preferably are oligonucleotides having a length of at least 10, in particular of at least 15 and particularly preferred of at least 50 nucleotides. The nucleic acid molecules and oligonucleotides of the invention can be used, for example, as primers for a PCR reaction. They can also be components of antisense constructs or of DNA molecules encoding suitable ribozymes.

The invention furthermore relates to vectors containing nucleic acid molecules of the invention. Preferably, they are plasmids, cosmids, viruses, bacteriophages and other vectors usually used in the field of genetic engineering.

Preferably, the nucleic acid sequence of the invention is operatively linked to the regulatory elements in the vector of the invention that guarantee the transcription and synthesis of an RNA in prokaryotic and/or eukaryotic cells that can be translated.

The expression vectors of the invention allow the production of enzymes synthesizing short-chain fructosyl polymers in various host organisms.

The encoded enzymes can be used also outside the host organisms for the production of short-chain fructosyl polymers. Thereby, fermentative and other biotechnological methods for the production of short-chain fructosyl polymers can be used. For example, it is also imaginable to produce fructosyl polymers by means of immobilized enzymes.

According to the invention regulatory elements of the patatin B33 promoter are preferred. Other preferred promoters are the 35S CaMV promoter and the promoter of the alcohol dehydrogenase gene from Saccharomyces cerevisiee.

The vectors of the invention can possess further functional units effecting the stabilization of the vector in the host organism, such as a bacterial replication origin or the 2μ DNA for the purpose of stabilization in Saccharomyces cerevisiae. Furthermore, "left border" and "right border" sequences of agrobacterial T-DNA can be contained, whereby a stable integration into the genome of plants is made possible.

Furthermore, the vectors of the invention can contain functional terminators, such as the terminator of the octopine synthase gene from agrobacteria.

In another embodiment the nucleic acid molecule of the invention is linked to the vector of the invention by a nucleic acid molecule encoding a functional signal sequence in order to transport the enzyme to various cell compartments. This modification can be, for example, the addition of an N-terminal signal sequence for secretion into the cell membrane space of higher plants but also any other modification that leads to the fusion of a signal sequence to the encoded fructosyltransferase can be the subject matter of the invention.

In a particularly preferred embodiment the invention relates to the plasmid pB33-cySST the construction of which is described in the examples (FIG. 1).

The expression of the nucleic acid molecules of the invention in prokaryotic cells, for example in *Escherichia coli*, is interesting because this way a closer characterization of the enzymatic activities of the enzymes encoding these molecules is possible.

In a further embodiment the invention relates to host cells transiently or stably containing the nucleic acid molecules or vectors of the invention. A host cell is understood to be an organism that is capable to take up in vitro recombinant DNA and, if the case may be, to synthesize the proteins encoded by the nucleic acid molecules of the invention.

Preferably, these cells are prokaryotic or eukaryotic cells. In particular, the invention relates to plant cells containing the vector systems of the invention or derivatives or parts therof. Preferably, they are able to synthesize enzymes for the production of short-chain fructosyl polymers due to the fact that they have taken up the vector systems of the invention, derivatives or parts thereof. The cells of the invention are preferably characterized by the fact that the introduced nucleic acid molecule of the invention either is heterologous with regard to the transformed cell, i.e. that it does not naturally occur in these cells, or is localized at a place in the genome different from that of the corresponding naturally occurring sequence.

A further embodiment of the invention relates to proteins being encoded by the nucleic acid molecules of the invention, as well as to methods for their production, whereby a host cell of the invention is cultivated under conditions allowing the synthesis of the protein and the protein is subsequently isolated from the cultivated cells and/or the culture medium. Furthermore, the invention relates to the SSTs that can be produced with the plants of the invention.

By providing the nucleic acid molecules of the invention it is now possible to produce short-chain fructosyl polymers in any organisms by means of genetic engineering, whereas up to now it had not been possible to modify plants by conventional methods, for example breeding methods, so that they are able to synthesize fructosyl polymers. By increasing the activity of the proteins of the invention, for example by overexpressing suitable nucleic acid molecules or by providing mutants that are no longer subject to the cell-specific regulation mechanisms and/or that have altered temperature dependencies with respect to their activity, it is possible to increase the yield in plants modified by genetic engineering.

Therefore, the expression of the nucleic acid molecules of the invention in plant cells in order to increase the activity of the corresponding SST or the introduction into cells normally not expressing this enzyme is now possible. Furthermore, it is possible to modify the nucleic acid molecules of the invention according to the methods known to the person skilled in the art in order to obtain SSTs of the invention that are no longer subject to the cell-specific regulation mechanisms or that have modified temperature dependencies or substrate or product specificities.

When the nucleic acid molecules are expressed in plants, the synthesized protein may be located in any compartment of the plant cell. In order to achieve the localization in a specific compartment, the sequence guaranteeing the localization in vacuole has to be deleted and, if necessary, the remaining coding region has to be linked to DNA sequences guaranteeing the localization in the specific compartment. Such sequences are known (see, e.g., Braun et al., EMBO J. 11 (1992), 3219–3227; Wolter et al., Proc. Natl. Acad. Sci. USA 85 (1988), 846–850; Sonnewald et al., Plant J. 1 (1991), 95–106). The present invention therefore also relates to transgenic plant cells that were transformed with one or several nucleotide molecule(s) of the invention as well as to transgenic plant cells originating from such transformed cells. Such cells contain one or several nucleic acid molecule (s) of the invention with it/them preferably being linked to regulatory DNA elements guaranteeing the transcription in plant cells, in particular with a promoter. Such plants can be distinguished from naturally occurring plant cells by the fact that they contain at least one nucleic acid molecule according to the invention which does not naturally occur in these cells or by the fact that such a molecule is integrated into the genome of the cell where it does not naturally occur, i.e. in another genomic region.

The transgenic plant cells can be regenerated to whole plants using methods known to the person skilled in the art. The subject matter of the present invention relates to the plants obtainable by regeneration of the transgenic plant cells of the invention. Furthermore, the subject matter of the invention relates to plants containing the transgenic plant cells described above. The transgenic plants can basically be plants of any plant species, i.e. both monocotyledonous and dikotyledonous plants. Preferably they are crops, in particular plants that synthesize and/or store starch, such as wheat, barley, rice, maize, sugar beet, sugar cane or potato. Particularly preferred are sucrose storing plants.

The invention also relates to propagation material and harvest products of the plants of the invention, for example fruits, seeds, tubers, root stocks, seedlings, cuttings etc.

The transgenic plant cells and plants of the invention synthesize short-chain fructosyl polymers due to the expression or additional expression of at least one nucleic acid molecule of the invention.

The subject matter of the invention therefore also relates to the short-chain fructosyl polymers obtainable from the transgenic plant cells and plants of the invention as well as from the propagation material and harvest products.

The transgenic plant cells of the invention can be regenerated to whole plants according to methods known to the person skilled in the art. Therefore, the subject matter of the invention also relates to plants containing the transgenic plant cells of the invention. These plants preferably are crops, in particular plants that synthesize and/or store sucrose and/or starch. Particularly preferred is potato. The invention also relates to the propagation material of the plants of the invention, in particular tubers.

In order to express the nucleic acid molecules of the invention in sense or antisense orientation in plant cells, they are linked to regulatory DNA elements guaranteeing the transcription in plant cells. These are particularly promoters. Basically, any promoter active in plant cells is suitable for the expression.

The promoter can be selected such that the expression takes place constitutively or only in a certain tissue, at a certain stage of the plant development or at a point of time determined by external stimuli. With regard to the plant the promoter can be homologous or heterologous. Suitable promoters are, for example, the promoter of the 35S RNA of the cauliflower mosaic virus and the ubiquitin promoter from maize for a constitutive expression, particularly preferred the patatin gen promoter B33 (Rocha-Sosa et al., EMBO J. 8 (1989), 23–29) for a tuber specific expression in potato or a promoter only guaranteeing the expression in photosynthetically active tissue, for example the ST-LS1 promoter (Stockhaus et al., Proc. Natl. Acad. Sci. USA 84 (1987), 7943–7947; Stockhaus et al., EMBO J. 8 (1989), 2445–2451) or for an endosperm specific expression the HMG promoters from wheat, the USP promoter, the Phaseolin promoter or promoters from zein genes from maize.

Furthermore, there can be a termination sequence serving for the correct termination of the transcription as well as the addition of a poly-A tail to the transcript which is regarded as having a function for the stabilization of the transcripts. Such elements are described in the literature (cf. Gielen et al., EMBO J. 8 (1989), 23–29) and can be exchanged arbitrarily.

In order to prepare the introduction of foreign genes into higher plants there is a great number of cloning vectors available containing a replication signal for $E.coli$ and a marker gene for the selection of transformed bacterial cells. Examples of such vectors are pBR322, pUC series, M13 mp series, pACYC184 etc. The desired sequence can be introduced into the vector at a suitable cleavage site. The plasmid obtained is suitable for the transformation of $E.coli$ cells. Transformed $E.coli$ cells are cultivated in a suitable medium, then harvested and lysed. The plasmid is regenerated. Usually, restriction analyses, gel electrophoreses and other biochemical or molecular biological methods are used as analysis methods for the characterization of the regenerated plasmid DNA. After every manipulation the plasmid DNA can be cleaved and the regenerated DNA fragments linked to other DNA sequences. Every plasmid DNA sequence can be cloned into the same or other plasmids.

For the introduction of DNA into a plant host cell a great number of methods are available. These methods comprise the transformation of plant cells with T-DNA using *Agrobacterium tumefaciens* or *Agrobacterium rhizogenes* as means for transformation, the fusion of protoplasts, the injection, the electroporation of DNA, the introduction of DNA by means of the biolistic methods as well as further possibilities. For the injection and electroporation of DNA in plant cells there are no specific requirements for the plasmids used. Simple plasmids such as pUC derivatives can be used. If whole plants are to be regenerated from such transformed cells, there should be a selectable marker.

Depending on the method for the introduction of desired genes into the plant cell further DNA sequences may be necessary. If, for example, the Ti or Ri plasmid is used for the transformation of the plant cell, at least the right border, often, however, the right and left border of the Ti and Ri plasmid T-DNA have to be linked as flanking region to the genes to be introduced.

If agrobacteria are used for the transformation, the DNA to be introduced has to be cloned into specific plasmids, either into an intermediary vector or into a binary vector. The intermediary vectors can be integrated into the Ti or Ri plasmid of the agrobacteria due to sequences that are homologous to sequences in the T-DNA by homologous recombination. The Ti or Ri plasmid furthermore contains the vir region necessary for the transfer of the T-DNA. Intermediary vectors cannot replicate in agrobacteria. By means of a helper plasmid the intermediary vector can be transferred to Agrobacterium tumefaciens (conjugation). Binary vectors can replicate both in $E.coli$ and in agrobacteria. They contain a selection marker gene and a linker or polylinker framed by the right and left T-DNA border region. They can be transformed directly into the agrobacteria (Holsters et al., Mol. Gen. Genet. 163 (1978), 181–187). The agrobacterium serving as a host cell should contain a plasmid carrying a vir region. The vir region is necessary for the transfer of the T-DNA into the plant cell. There may be additional T-DNA. The agrobacterium transformed such is used for the transformation of plant cells. The use of T-DNA for the transformation of plant cells has extensively been examined and described in EP-A-120 516; Hoekema: The Binary Plant Vector System, Offsetdrukkerij Kanters B. V., Alblasserdam (1985), Chapter V, Fraley et al., Crit. Rev. Plant. Sci., 4, 1–46 and An et al., EMBO J. 4 (1985), 277–287. For the transfer of the DNA into the plant cell plant explants can be co-cultivated with Agrobacterium tumefaciens or Agrobacterium rhizogenes. From the infected plant material (e.g., pieces of leaf, stem segments, roots, but also protoplasts or plant cells cultivated by suspension) whole plants can be regenerated in a suitable medium, which may contain antibiotics or biozides for the selection of transformed cells. The plants obtained this way can be examined for the presence of the introduced DNA. Other possibilities of introducing foreign DNA using the biolistic methods or by protoplast transformation are known (cf., e.g., Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627–659, VCH Weinheim-New York-Basel-Cambridge).

Alternative systems for the transformation of monocotyledonous plants are the transformation by means of the biolistic approach, the electrically or chemically induced introduction of DNA into protoplasts, the electroporation of partially permeabilized cells, the macroinjection of DNA into flowers, the microinjection of DNA into microspores and pro-embryos, the introduction of DNA into germinating pollen and the introduction of DNA into embryos by swelling (for review: Potrykus, Physiol. Plant (1990), 269–273).

While the transformation of dicotyledonous plants via Ti plasmid vector systems with the help of Agrobacterium tumefaciens is well-established, more recent research work indicates that also monocotyledonous plants are accessible for transformation by means of vectors based on Agrobacterium (Chan et al., Plant Mol. Biol. 22 (1993), 491–506; Hiei et al., Plant J. 6 (1994), 271–282; Bytebier et al., Proc. Natl. Acad. Sci. USA 84 (1987), 5345–5349; Raineri et al., Bio/Technology 8 (1990), 33–38; Gould et al., Plant Physiol. 95 (1991), 426434; Mooney et al., Plant, Cell Tiss. & Org. Cult. 25 (1991), 209–218; Li et al., Plant Mol. Biol. 20 (1992), 1037–1048).

Three of the above-mentioned transformation systems could be established for various cereals: the electroporation of tissues, the transformation of protoplasts and the DNA transfer by particle bombardment in regenerative tissue and cells (for review: Jähne et al., Euphytica 85 (1995), 35–44).

The transformation of wheat has been frequently described in the literature (for review: Maheshwari et al., Critical Reviews in Plant Science 14 (2) (1995), 149–178).

The invention also relates to plants containing at least one, preferably a number of cells containing the vector systems of the invention or derivatives or parts thereof and being able to synthesize enzymes for the production of short-chain fructosyl polymers due to the introduction of the vector systems, derivatives or parts of the vector systems of the invention. The invention also provides plants of many species, genuses, families, orders and classes that are able to synthesize enzymes for the production of short-chain fructosyl polymers due to the introduced vector systems or derivatives or parts thereof. Since the known plants are not able to only produce short-chain fructosyl polymers, it is easy to check whether the method has been successfully performed, for example by chromatographic analysis of the sugars containing fructose. They are advantageous vis-à-vis the few plants containing fructosyl polymers since there is a defined molecular size, i.e. the size of the short-chain fructosyl polymer. Furthermore, a localization in the various cell compartments and various organs as well as an increase of the expression ratio and therefore of the yield is possible.

In another embodiment the invention relates to method s for the production of short-chain fructosyl polymers comprising:

(a) contacting sucrose or an equivalent substrate with an SST of the invention under conditions allowing the conversion to short-chain fructosyl polymers; and (b) obtaining the fructosyl polymers produced this way.

The nature of the produced fructosyl polymers depends on the enzymatic specificity of the fructosyl transferase. When an SST of the invention is used, preferably kestose but also nystose and fructosylnystose are produced.

Furthermore, the invention relates to the fructosyl polymers produced from a plant cell or plant of the invention or from the propagation material or harvest product of plants or plant cells of the invention or obtained according to the above-described method of the invention. These fructosyl polymers can preferably be used for the production of food such as baked goods or pasta. Preferably, these fructosyl polymers can be used for increasing the viscosity in aqueous systems, as detergents, as suspending agents or for accelerating the sedimentation process and complexing but also for binding water.

Vector: pBinB33 (derivative of pBin19; Bevan, 1984, Nucl Acids Res 12: 8711)

promoter: B33 promoter (Rocha-Sosa et al., 1989, EMBO J 8: 23–29)

donor: *Solanum tuberosum* coding region: SST gene from *Cynars scolymus* orientation: sense terminator: Polyadenylation signal of the octopin synthase gene from *A. tumefaciens* plasmid pTiACH5 (Gielen et al., 1984, EMBO J 3: 835–846)

donator: *Agrobacterium tumefaciens* resistance: kanamycin

Figure 2:
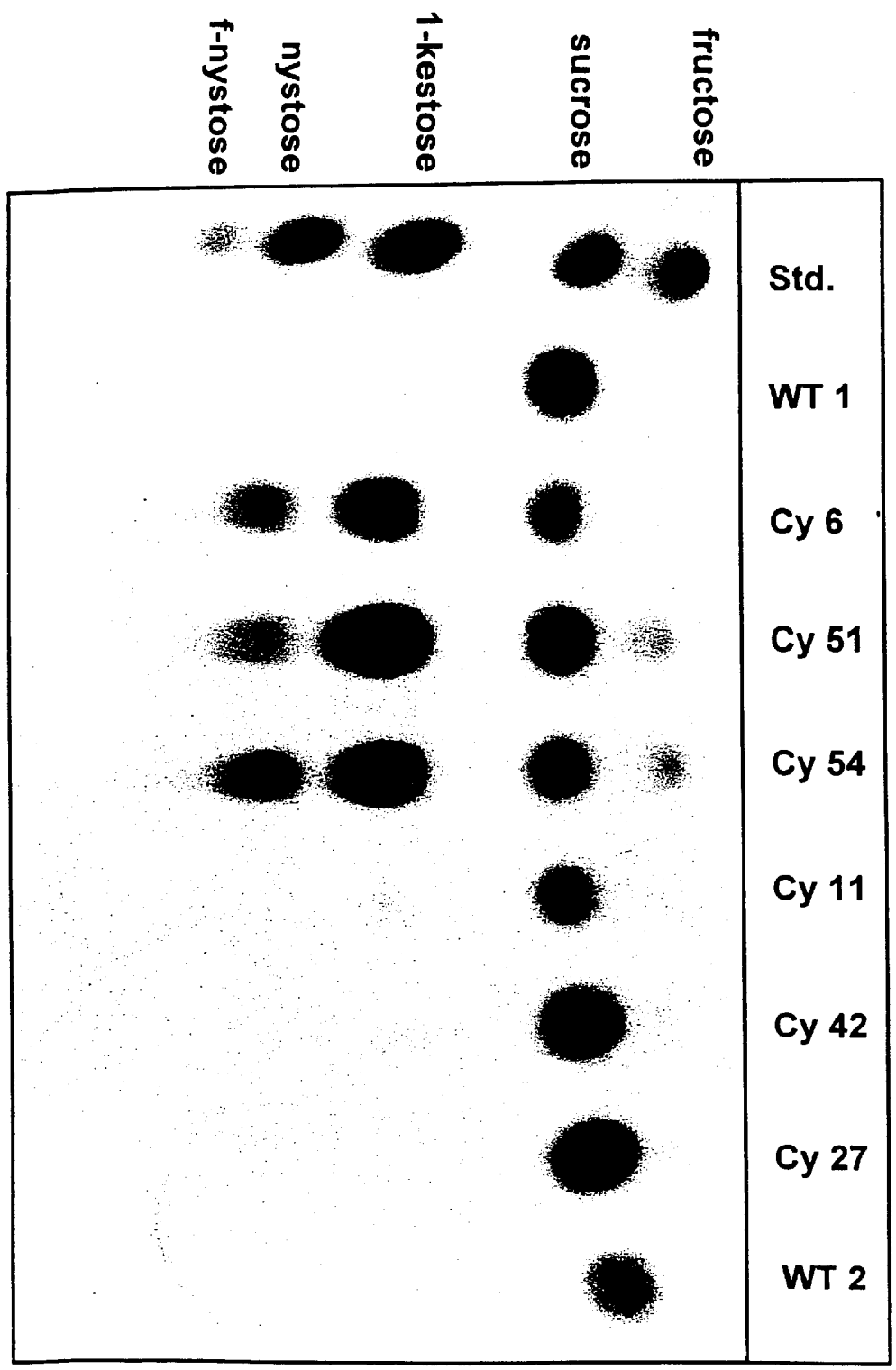

FIG. 2 shows the analysis of the soluble sugars in the tubers of transgenic plants that were produced using the vector system pB33-cySST. The short-chain fructosyl polymers (in particular 1-kestose) produced due to the genetic modification have been labeled.

Figure 3A:
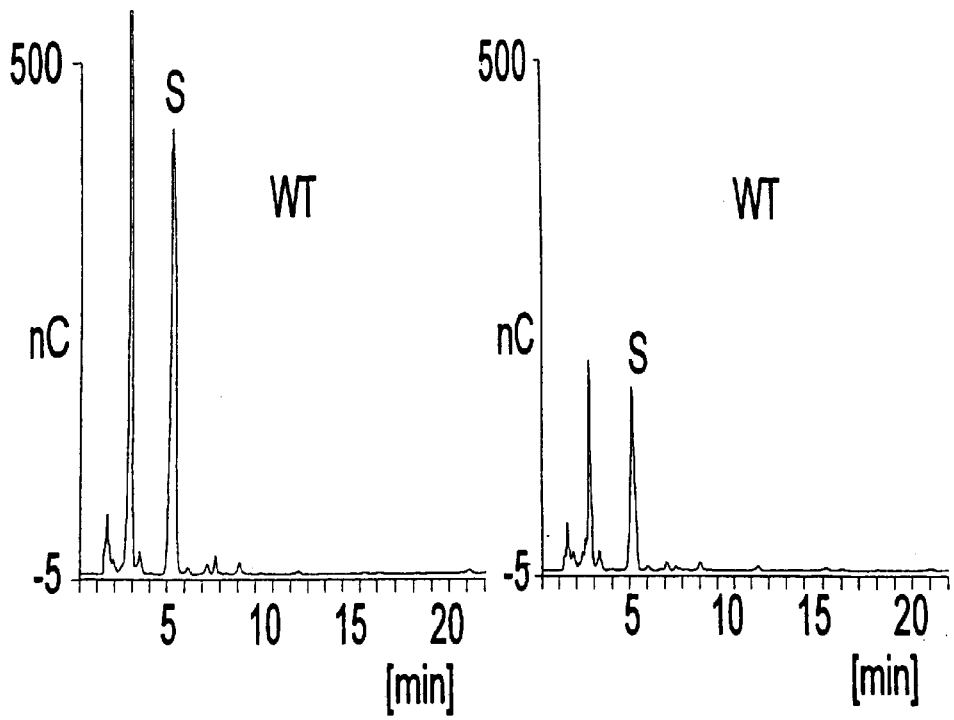
Figure 3B:
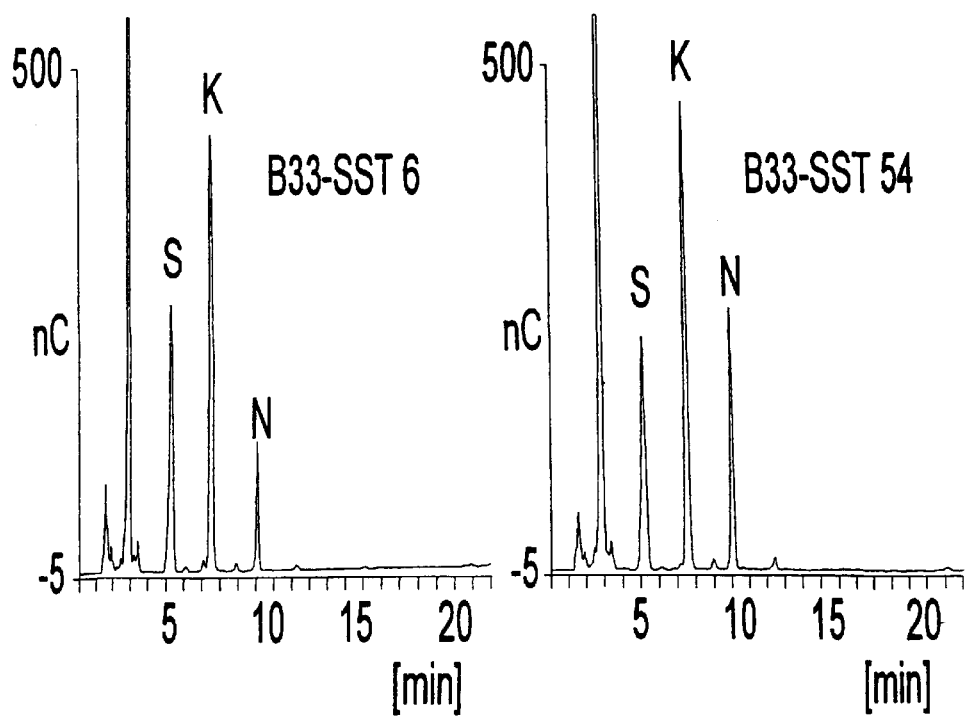
Figure 3C:
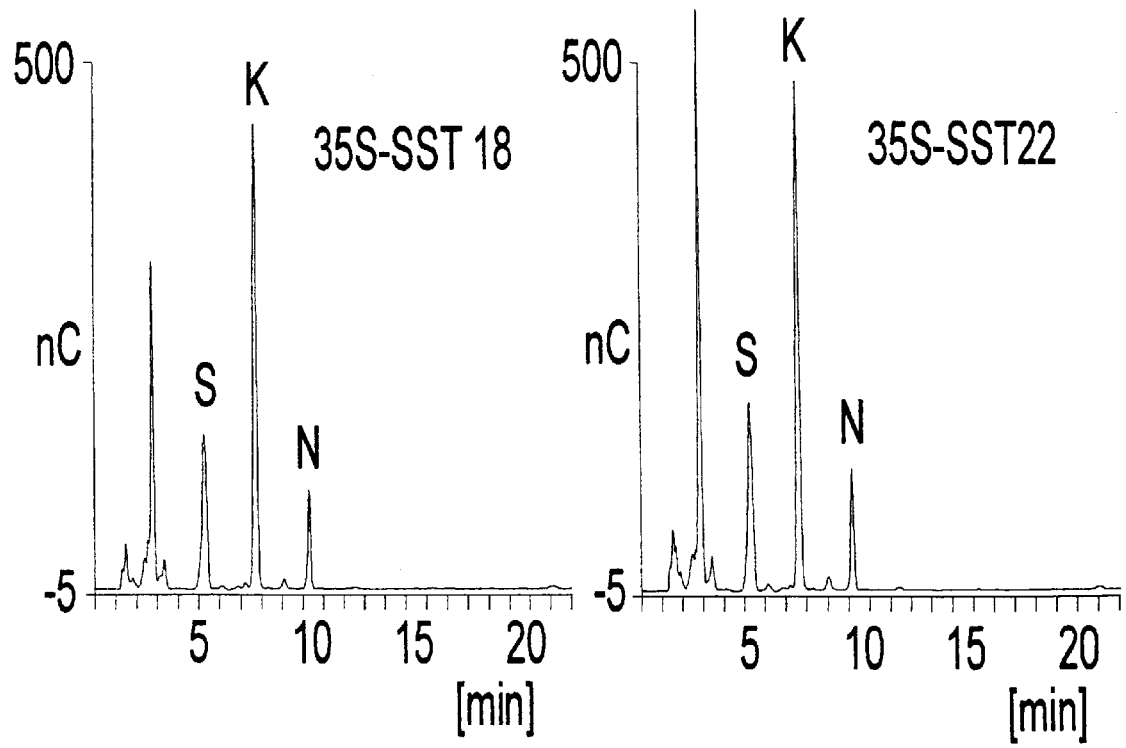

FIGS. 3A–3C show the analysis of the soluble sugars in transgenic plants that were produced using the vector system pB33-cySST and p35S-cySST, respectively, compared to wildtype plants.

DETAILED DESCRIPTION OF THE INVENTION

Example 1

Identification, Isolation and Characterization of a cDNA Encoding a Sucrose Dependent Sucrose-fructosyltransferase from Artichoke (*Cynare scolymus*)

Total RNA-was isolated from blossom discs of artichoke (Sambrook et al., see supra). Poly(A)$^+$mRNA was isolated using the mRNA isolation system PolyATtract (Promega Corporation, Madison, Wis., USA). Complementary DNA (cDNA) was produced from 5 $\mu$g of this RNA by means of the ZAp-cDNA synthesis kit of Stratagene according to the manufacturer's instructions. 2×10$^6$ independent recombinant phages were obtained. The amplified cDNA library was screened by conventional methods with a DNA fragment labeled with $^{32}$p and corresponding to the 3'-terminal of the 6-SFT cDNA (Sprenger et al., Proc. Natl. Acad. Sci. USA 92 (1995), 11652) having a length of 392 bp. This fragment was obtained from the complete RNA by RT-PCR (RT-PCR Kit, Stratagene, Heidelberg, Germany) as matrix from light-induced (72 hours) primary leaves from barley. Positive clones were further examined.

EXAMPLE 2

Sequence Analysis of the cDNA Insertion of the Plasmid pCy21

The plasmid DNA was isolated from the clone pCy21. The sequence of the cDNA insertion was determined by conventional methods by means of the dideoxynucleotide method (Sanger et al., Proc. Natl. Acad. Sci USA 74 (1977), 5463–5467).

The insertion of the clone pCy21is a DNA of 2055 bp. The nucleotide sequence is depicted in Seq ID No. 1. The corresponding amino acid sequence is depicted in Seq ID No. 2.

A sequence analysis and a comparison with already published sequences showed that the sequence depicted in Seq ID No. 1 is novel and comprises a coding region showing homologies to SSTs from other organisms.

EXAMPLE 3

Figure 1:
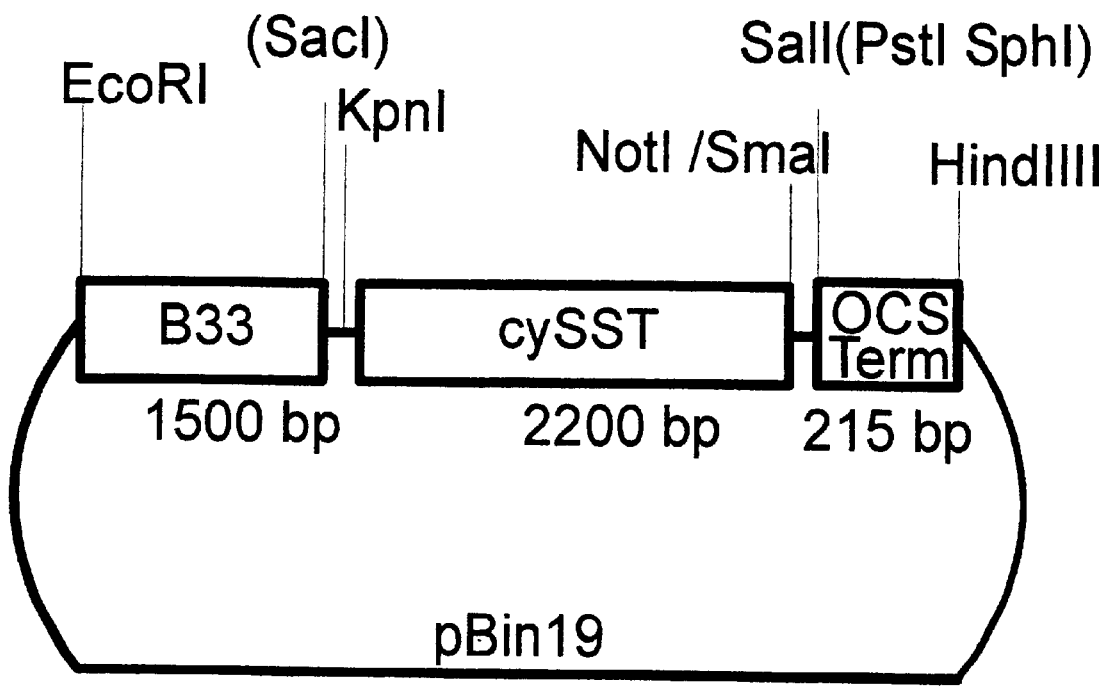
FIG. 1 shows the construction of the plasmid pB33-cySST.

Production of the Plasmid pB33-cySST and Introduction of the Plasmid into the Genome of Potato The plasmid pB33-cySST contains three fragments A, B and C in the binary vector pBin19 (Bevan, 1984, Nucl Acids Res 12: 8711, modified according to Becker, 1990, Nucl Acids Res 18: 203) (cf. FIG. 1). Fragment A contains the B33 promoter of the patatin gene b33 of potato. It contains a DraI fragment (position −1512 to position +14) of the patatin gene B33 (Rocha-Sosa et al., 1989, EMBO J 8:23–29), which is inserted between the EcoRI and the SacI cleavage site of the polylinker of pBin19-Hyg. Fragment B contains the coding region of the sequence depicted in SEQ ID No. 1. Fragment B was obtained as NotI fragment with blunt ends from the vector pBluescript SK, in which it is inserted into the EcoRI cleavage site via an EcoRI/NotI linker sequence. Fragment C contains the polyadenylation signal of the gene 3 of the T-DNA of the Ti plasmid pTi ACH 5 (Gielen et al (1984); EMBO J. 3, 835–846) nucleotides 11749–11939, which was isolated as Pvu II-Hind III fragment from the plasmid pAGV 40 (Herrera-Estrella et al (1983) Nature 303, 209–213) and cloned between the SphI and the Hind III cleavage site of the polylinker of pbin 19-Hyg after the addition of SphI linkers to the Pvu II cleavage site. The plasmid pB33-cySST has a size of approx. 14 kb. The plasmid was introduced into agrobactelia (H öfgen and Willmitzer, Nucleic Acids Res. 16 (1988), 9877).

The plasmid pB33-cySST was introduced into potato plants via the gene transfer induced by Agrobacterium according to the above-described conventional methods. Intact plants were regenerated from transformed cells. From regenerated plants enzyme extracts were obtained and examined for the presence of fructosyl polymers. The analysis was carried out as described in Röber (Planta 199, 528–536). The analysis of the tubers of a number of transformed plants transformed with this vector clearly showed the presence of short-chain fructosyl polymers, in particular 1-kestose, which can be put down to the expression of the SST gene of the invention (cf. FIG. 2).

EXAMPLE 4

Analysis of Soluble Sugar in Wildtype and SST Containing Transgenic Plants

Transgenic plants containing vectors pB33-cySST and 35S-cySST (having the coding region of SEQ ID No. 1 under the control of the 35S promoter) were generated as described in Example 3. Extracts were obtained from transgenic plants and wildtype plants and examined for the presence of fructosyl polymers; see Example 3. HPAEC-analysis shown in FIG. 3 demonstrates the production of oligofructanes. The results are summarized in Table 1, below.

TABLE 1

Soluble sugars (sucrose and oligofructane) in wildtype and transgenic plants

| line | sucrose | 1-kestose | nystose | F-nystose |
|---|---|---|---|---|
| WT 1 (Désirée) | 2,09 | — | — | — |
| WT 2 (Désirée) | 1,67 | — | — | — |
| B33-cySST 6 | 2,26 | 3,58 | 1,60 | — |
| B33-cySST 54 | 5,13 | 3,06 | 2,90 | 0,23 |
| 35S-cySST 18 | 4,08 | 4,05 | 1,51 | 0,12 |
| 35S-CySST 22 | 4,80 | 4,14 | 2,19 | <0,1 |

Values in g carbohydrate per kg fresh weight

As is evident from FIG. 3 and Table 1, supra, the content of fructosyl polymers, in particular 1-kestose exceeds the content of sucrose. Thus, the experiments performed in accordance with the present invention demonstrate the usefulness of the nucleic acid molecules of the invention for the production of fructosyl polymers in transgenic plants.

---

We claim:

1. An isolated nucleic acid molecule comprising a nucleic acid sequence encoding a sucrose dependent sucrose fructosyltransferase (SST), selected from the group consisting of:
   (a) a nucleic acid sequence encoding a protein comprising the amino acid sequence of SEQ ID NO: 2 or SEQ ID NO: 4;
   (b) a nucleic acid sequence comprising the nucleotide sequence of SEQ ID NO: 1 or a corresponding ribonucleotide sequence;
   (c) a nucleic acid sequence comprising the nucleotide sequence of SEQ ID NO: 3 or a corresponding ribonucleotide sequence; and
   (d) a nucleic acid sequence comprising a fragment of the nucleic acid sequence of any one of subsections (a) to (c), said fragment encoding a protein that catalyzes a β-2,1-glycosidic linkage or β-2,6-glycosidic linkage between fructose units.

2. The nucleic acid molecule according to claim 1 which is a DNA molecule.

3. The DNA molecule according to claim 2, which is a cDNA molecule.

4. The nucleic acid molecule according to claim 1, which is an RNA molecule.

5. A vector comprising the nucleic acid molecule according to claim 1.

6. The vector according to claim 5, wherein the nucleic acid molecule is operatively linked to regulatory elements allowing the transcription and synthesis of an RNA translatable in prokaryotic or eukaryotic cells or translatable in prokarvotic and eukaryotic cells.

7. The vector according to claim 6, wherein the regulatory elements are derived from the patatin B33 promoter.

8. A host cell into which the nucleic acid molecule according to claim 1 or a vector comprising said nucleic acid molecule has been introduced, or a derivative of said host cell, wherein said derivative comprises said nucleic acid molecule.

9. A method for the production of an SST comprising:

cultivating the host cell according to claim 8 under conditions allowing the synthesis of the SST and isolating the SST from the cultivated cells, a culture medium comprising the cultivated cells, or the cultivated cells and the culture medium.

10. A transgenic plant cell comprising the nucleic acid molecule according to claim 1 or a vector comprising said nucleic acid molecule, or a derivative of said transgenic plant cell, wherein said derivative comprises the nucleic acid molecule, and wherein the nucleic acid molecule is controlled by regulatory elements allowing the transcription of a translatable mRNA in the plant cell, or the derivative thereof.

11. A plant comprising the plant cell according to claim 10.

12. The plant according to claim 11, which is a crop plant.

13. The plant according to claim 12, which is a sucrose or starch-storing plant.

14. The plant according to claim 13, which is a potato plant.

15. Propagation material comprising the plant cell according to claim 10.

16. A harvest product of a plant, comprising the plant cell of claim 10.

17. A method for production of short-chain fructosyl polymers comprising:

(a) cultivating the plant according to any one of claims 11 to 14; and (b) obtaining the fructosyl polymers from the plant, its propagation material, or its harvest product.

18. The plant according to claim 11, which is a wheat, barley, rice, maize, sugar beet, sugar cane, or potato plant.

19. An isolated nucleic acid molecule comprising a nucleic acid sequence encoding a sucrose dependent fructosyltransferase (SST), which is at least 90% identical to the amino acid sequence of SEQ ID NO: 2.

20. A fragment of an isolated nucleic acid molecule according to claim 19, wherein the fragment encodes a protein that catalzes a $\beta$-2,1-glycosidic linkage between fructose units.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 2226 base pairs
      (B) TYPE: nucleotide
      (C) STRANDEDNESS: single
      (D) TOPOLOGY: linear (ii) MOLECULE TYPE: cDNA (vi) ORIGINAL SOURCE:
      (A) ORGANISM: Cynara Scolymus (ix) FEATURE:
      (A) NAME/KEY: CDS
      (B) LOCATION: 8..1918

(xi) SEQUENCE DESCRIPTION: SEQ ID NO: 1:

```
CCACCAC ATG GCT TCC TCT ACC ACC ACC CCA CTC CTC CCT CAC CAC CAC        49
        Met Ala Ser Ser Thr Thr Thr Pro Leu Leu Pro His His His
         1               5                      10

CTT CAG AAC CCG CAA CAA CTC GCC GGA TCT CCG GCA GCT CAT CGT CTA        97
Leu Gln Asn Pro Gln Gln Leu Ala Gly Ser Pro Ala Ala His Arg Leu
 15              20                  25                      30

TCC CGA CCC ACA CTC CTT TCT GGG ATC CTT GTT TCG GTC CTA GTC ATC       145
Ser Arg Pro Thr Leu Leu Ser Gly Ile Leu Val Ser Val Leu Val Ile
                 35                  40                  45

TGT GCT CTC GTT GCT GTA ATC CAC AAC CAA TCA CAG CAA CCC TAC CAT       193
Cys Ala Leu Val Ala Val Ile His Asn Gln Ser Gln Gln Pro Tyr His
             50                  55                  60

GAC GGC GGA GCT AAA CCC TCC TCC TCC GCC GCT ACC ACC ACC TTC CCA       241
Asp Gly Gly Ala Lys Pro Ser Ser Ser Ala Ala Thr Thr Thr Phe Pro
         65                  70                  75

ACA GCG TCG CCA GAA GCT GGT TTG AAA CGG TTT CCC ATT GAG TTG AAA       289
Thr Ala Ser Pro Glu Ala Gly Leu Lys Arg Phe Pro Ile Glu Leu Lys
     80                  85                  90

ACG AAT GCT GAG GTT GAG TGG CAA CGC TCG GCT TAC CAT TTT CAG CCC       337
Thr Asn Ala Glu Val Glu Trp Gln Arg Ser Ala Tyr His Phe Gln Pro
 95                 100                 105                 110

GAT AAG AAC TAC ATT AGC GAT CCT GAT GGC CCA ATG TAT CAC ATG GGG       385
Asp Lys Asn Tyr Ile Ser Asp Pro Asp Gly Pro Met Tyr His Met Gly
                115                 120                 125

TGG TAT CAT CTC TTC TAT CAG TAC AAT CCA GAG TCT GCC ATC TGG GGG       433
Trp Tyr His Leu Phe Tyr Gln Tyr Asn Pro Glu Ser Ala Ile Trp Gly
            130                 135                 140

AAC ATC ACA TGG GGC CAC TCC GTA TCC AAA GAC ATG ATC AAC TGG TTC       481
Asn Ile Thr Trp Gly His Ser Val Ser Lys Asp Met Ile Asn Trp Phe
        145                 150                 155

CAT CTC CCC TTC GCC ATG GTC CCT GAC CAA TGG TAC GAT ATC GAA GGT       529
His Leu Pro Phe Ala Met Val Pro Asp Gln Trp Tyr Asp Ile Glu Gly
    160                 165                 170

GTC ATG ACC GGC TCC GCC ACC GTC CTC CCT GAC GGT CAG ATC ATC ATG       577
Val Met Thr Gly Ser Ala Thr Val Leu Pro Asp Gly Gln Ile Ile Met
175                 180                 185                 190

CTC TAC ACC GGC AAC GCG TAC GAT CTC TCG CAA CTG CAA TGC TTA GCA       625
Leu Tyr Thr Gly Asn Ala Tyr Asp Leu Ser Gln Leu Gln Cys Leu Ala
                195                 200                 205

TAT GCC GTC AAC TCG TCT GAT CCC CTC CTC CTC GAT TGG AAA AAG TAC       673
Tyr Ala Val Asn Ser Ser Asp Pro Leu Leu Leu Asp Trp Lys Lys Tyr
            210                 215                 220

GAG GGA AAT CCC ATC TTG TTC CCA CCT CCT GGG GTG GGA TAC AAG GAT       721
Glu Gly Asn Pro Ile Leu Phe Pro Pro Pro Gly Val Gly Tyr Lys Asp
        225                 230                 235

TTT CGG GAC CCA TCT ACA CTG TGG TTG GGT CCC GAT GGT GAA TAC AGA       769
Phe Arg Asp Pro Ser Thr Leu Trp Leu Gly Pro Asp Gly Glu Tyr Arg
    240                 245                 250

ATG GTA ATG GGG TCC AAG CAT AAC GAG ACC ATC GGT TGT GCC TTG ATT       817
Met Val Met Gly Ser Lys His Asn Glu Thr Ile Gly Cys Ala Leu Ile
255                 260                 265                 270

TAC CAT ACC ACT AAT TTT ACG CAT TTC GAG CTC AAG GAA GAG GTG CTT       865
Tyr His Thr Thr Asn Phe Thr His Phe Glu Leu Lys Glu Glu Val Leu
                275                 280                 285

CAC GCC GTT CCC CAC ACG GGT ATG TGG GAA TGT GTG GAT CTT TAT CCG       913
His Ala Val Pro His Thr Gly Met Trp Glu Cys Val Asp Leu Tyr Pro
            290                 295                 300

GTA TCC ACC ACG CAC ACA AAC GGG TTG GAC ATG GTG GAT AAC GGG CCG       961
Val Ser Thr Thr His Thr Asn Gly Leu Asp Met Val Asp Asn Gly Pro
```

-continued

```
         305                 310                 315
AAT GTG AAG CAT GTG TTG AAA CAA AGT GGG GAT GAA GAT CGA CAT GAT    1009
Asn Val Lys His Val Leu Lys Gln Ser Gly Asp Glu Asp Arg His Asp
    320                 325                 330

TGG TAT GCG CTC GGG ACT TAT GAC GTC GTG AAT GAT AAG TGG TAT CCA    1057
Trp Tyr Ala Leu Gly Thr Tyr Asp Val Val Asn Asp Lys Trp Tyr Pro
335                 340                 345                 350

GAT GAC CCT GAA AAC GAT GTG GGT ATC GGG TTA AGA TAC GAT TTC GGA    1105
Asp Asp Pro Glu Asn Asp Val Gly Ile Gly Leu Arg Tyr Asp Phe Gly
                355                 360                 365

AAG TTT TAT GCG TCA AAG ACG TTC TAC GAC CAA CAT AAG AAG AGA CGG    1153
Lys Phe Tyr Ala Ser Lys Thr Phe Tyr Asp Gln His Lys Lys Arg Arg
            370                 375                 380

GTC CTT TGG GGT TAC GTT GGA GAA ACC GAT CCC CCT AAA TAC GAC GTT    1201
Val Leu Trp Gly Tyr Val Gly Glu Thr Asp Pro Pro Lys Tyr Asp Val
        385                 390                 395

TAC AAG GGA TGG GCT AAC ATT TTG AAC ATT CCA AGG ACC ATA GTT TTG    1249
Tyr Lys Gly Trp Ala Asn Ile Leu Asn Ile Pro Arg Thr Ile Val Leu
    400                 405                 410

GAC ACG AAA ACG AAT ACC AAT TTG ATT CAA TGG CCA ATT GCG GAA GTC    1297
Asp Thr Lys Thr Asn Thr Asn Leu Ile Gln Trp Pro Ile Ala Glu Val
415                 420                 425                 430

GAA AAC TTG AGA TCG AAT AAA TAC AAT GAA TTC AAA GAC GTG GAG CTG    1345
Glu Asn Leu Arg Ser Asn Lys Tyr Asn Glu Phe Lys Asp Val Glu Leu
                435                 440                 445

AAA CCG GGA TCA CTG ATT CCG CTC GAG ATA GGC ACA GCA ACA CAG TTG    1393
Lys Pro Gly Ser Leu Ile Pro Leu Glu Ile Gly Thr Ala Thr Gln Leu
            450                 455                 460

GAT ATA ACT GCG ACA TTC GAA GTT GAT CAA ACG ATG TTG GAA TCG ACG    1441
Asp Ile Thr Ala Thr Phe Glu Val Asp Gln Thr Met Leu Glu Ser Thr
        465                 470                 475

CTT GAA GCC GAT GTT TTG TTC AAT TGT ACG ACC AGT GAA GGT TCA GCC    1489
Leu Glu Ala Asp Val Leu Phe Asn Cys Thr Thr Ser Glu Gly Ser Ala
    480                 485                 490

GGG AGA GGG GTG TTG GGG CCA TTT GGA CTG GTG GTT CTA GCT GAT GCC    1537
Gly Arg Gly Val Leu Gly Pro Phe Gly Leu Val Val Leu Ala Asp Ala
495                 500                 505                 510

GAA CGA TCT GAG CAA CTT CCT GTG TAT TTC TAT ATA GCA AAA GAC ACC    1585
Glu Arg Ser Glu Gln Leu Pro Val Tyr Phe Tyr Ile Ala Lys Asp Thr
                515                 520                 525

GAT GGA TCC TCA AAA ACT TAC TTC TGT GCC GAT GAA TCA AGA TCA TCG    1633
Asp Gly Ser Ser Lys Thr Tyr Phe Cys Ala Asp Glu Ser Arg Ser Ser
            530                 535                 540

AAC GAT GTA GAC ATA GGG AAA TGG GTG TAC GGA AGC AGT GTT CCT GTT    1681
Asn Asp Val Asp Ile Gly Lys Trp Val Tyr Gly Ser Ser Val Pro Val
        545                 550                 555

CTA GAA GGC GAA AAA TTC AAC ATG AGG TTG CTG GTG GAT CAT TCA ATT    1729
Leu Glu Gly Glu Lys Phe Asn Met Arg Leu Leu Val Asp His Ser Ile
    560                 565                 570

GTC GAA GGC TTC GCA CAA GGA GGC AGA ACG GTG GTG ACA TCA AGA GTG    1777
Val Glu Gly Phe Ala Gln Gly Gly Arg Thr Val Val Thr Ser Arg Val
575                 580                 585                 590

TAT CCG GCG AAG GCG ATC TAC GGC GCT GCA AAG TTA TTT TTG TTC AAC    1825
Tyr Pro Ala Lys Ala Ile Tyr Gly Ala Ala Lys Leu Phe Leu Phe Asn
                595                 600                 605

AAC GCC ACC GGA ATC AGC GTG AAG GCA TCT CTC AAG ATC TGG AAA ATG    1873
Asn Ala Thr Gly Ile Ser Val Lys Ala Ser Leu Lys Ile Trp Lys Met
            610                 615                 620

AAG GAA GCA CAA CTG GAT CCA TTC CCT CTT TCT GGA TGG AGT TCT        1918
```

```
Lys Glu Ala Gln Leu Asp Pro Phe Pro Leu Ser Gly Trp Ser Ser
            625                 630                 635

TGATGATGAT GATGATTAAG AACTCATTTC ATGAAGATGA TGATTAAGAA CTCATTTCAT    1978

GATGATGATG ATGATTCCAG TTTATATGCG TACCCTGTTC CCTTTACCTG TATGTGGTGG    2038

TGGTGGTGAA ATATGGTTAG CATGATTCCG GGTTGGCGAG GGCAATATGG TAATTTACTA    2098

TCGCTGTAGT AGTACTCCAC TTGTGAGATT ATATTTCATA AATTCAATTA TTATTCCTGT    2158

TTACAACCTT TTTCATTGTA TCATACCACC CATTGAATCC CATCATGTTC AATTAGTGTT    2218

GCAAAAAA                                                              2226

(2) INFORMATION FOR SEQ ID NO: 2:

(i) SEQUENCE CHARACTERISTICS:
        (A) LENGTH: 637 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Ser Ser Thr Thr Thr Pro Leu Leu Pro His His Leu Gln
  1               5                  10                  15

Asn Pro Gln Gln Leu Ala Gly Ser Pro Ala Ala His Arg Leu Ser Arg
                 20                  25                  30

Pro Thr Leu Leu Ser Gly Ile Leu Val Ser Val Leu Val Ile Cys Ala
            35                  40                  45

Leu Val Ala Val Ile His Asn Gln Ser Gln Gln Pro Tyr His Asp Gly
      50                  55                  60

Gly Ala Lys Pro Ser Ser Ser Ala Ala Thr Thr Thr Phe Pro Thr Ala
 65                  70                  75                  80

Ser Pro Glu Ala Gly Leu Lys Arg Phe Pro Ile Glu Leu Lys Thr Asn
                 85                  90                  95

Ala Glu Val Glu Trp Gln Arg Ser Ala Tyr His Phe Gln Pro Asp Lys
            100                 105                 110

Asn Tyr Ile Ser Asp Pro Asp Gly Pro Met Tyr His Met Gly Trp Tyr
        115                 120                 125

His Leu Phe Tyr Gln Tyr Asn Pro Glu Ser Ala Ile Trp Gly Asn Ile
    130                 135                 140

Thr Trp Gly His Ser Val Ser Lys Asp Met Ile Asn Trp Phe His Leu
145                 150                 155                 160

Pro Phe Ala Met Val Pro Asp Gln Trp Tyr Asp Ile Glu Gly Val Met
                165                 170                 175

Thr Gly Ser Ala Thr Val Leu Pro Asp Gly Gln Ile Ile Met Leu Tyr
            180                 185                 190

Thr Gly Asn Ala Tyr Asp Leu Ser Gln Leu Gln Cys Leu Ala Tyr Ala
        195                 200                 205

Val Asn Ser Ser Asp Pro Leu Leu Leu Asp Trp Lys Lys Tyr Glu Gly
    210                 215                 220

Asn Pro Ile Leu Phe Pro Pro Gly Val Gly Tyr Lys Asp Phe Arg
225                 230                 235                 240

Asp Pro Ser Thr Leu Trp Leu Gly Pro Asp Gly Glu Tyr Arg Met Val
                245                 250                 255

Met Gly Ser Lys His Asn Glu Thr Ile Gly Cys Ala Leu Ile Tyr His
            260                 265                 270

Thr Thr Asn Phe Thr His Phe Glu Leu Lys Glu Glu Val Leu His Ala
```

```
                    275                 280                 285
Val Pro His Thr Gly Met Trp Glu Cys Val Asp Leu Tyr Pro Val Ser
    290                 295                 300

Thr Thr His Thr Asn Gly Leu Asp Met Val Asp Asn Gly Pro Asn Val
305                 310                 315                 320

Lys His Val Leu Lys Gln Ser Gly Asp Glu Asp Arg His Asp Trp Tyr
                325                 330                 335

Ala Leu Gly Thr Tyr Asp Val Val Asn Asp Lys Trp Tyr Pro Asp Asp
                340                 345                 350

Pro Glu Asn Asp Val Gly Ile Gly Leu Arg Tyr Asp Phe Gly Lys Phe
                355                 360                 365

Tyr Ala Ser Lys Thr Phe Tyr Asp Gln His Lys Lys Arg Arg Val Leu
    370                 375                 380

Trp Gly Tyr Val Gly Glu Thr Asp Pro Pro Lys Tyr Asp Val Tyr Lys
385                 390                 395                 400

Gly Trp Ala Asn Ile Leu Asn Ile Pro Arg Thr Ile Val Leu Asp Thr
                405                 410                 415

Lys Thr Asn Thr Asn Leu Ile Gln Trp Pro Ile Ala Glu Val Glu Asn
                420                 425                 430

Leu Arg Ser Asn Lys Tyr Asn Glu Phe Lys Asp Val Glu Leu Lys Pro
            435                 440                 445

Gly Ser Leu Ile Pro Leu Glu Ile Gly Thr Ala Thr Gln Leu Asp Ile
    450                 455                 460

Thr Ala Thr Phe Glu Val Asp Gln Thr Met Leu Glu Ser Thr Leu Glu
465                 470                 475                 480

Ala Asp Val Leu Phe Asn Cys Thr Thr Ser Glu Gly Ser Ala Gly Arg
                485                 490                 495

Gly Val Leu Gly Pro Phe Gly Leu Val Val Leu Ala Asp Ala Glu Arg
                500                 505                 510

Ser Glu Gln Leu Pro Val Tyr Phe Tyr Ile Ala Lys Asp Thr Asp Gly
                515                 520                 525

Ser Ser Lys Thr Tyr Phe Cys Ala Asp Glu Ser Arg Ser Ser Asn Asp
    530                 535                 540

Val Asp Ile Gly Lys Trp Val Tyr Gly Ser Ser Val Pro Val Leu Glu
545                 550                 555                 560

Gly Glu Lys Phe Asn Met Arg Leu Leu Val Asp His Ser Ile Val Glu
                565                 570                 575

Gly Phe Ala Gln Gly Gly Arg Thr Val Val Thr Ser Arg Val Tyr Pro
                580                 585                 590

Ala Lys Ala Ile Tyr Gly Ala Ala Lys Leu Phe Leu Phe Asn Asn Ala
    595                 600                 605

Thr Gly Ile Ser Val Lys Ala Ser Leu Lys Ile Trp Lys Met Lys Glu
610                 615                 620

Ala Gln Leu Asp Pro Phe Pro Leu Ser Gly Trp Ser Ser
625                 630                 635
```

(2) INFORMATION FOR SEQ ID NO: 3:

(i) SEQUENCE CHARACTERISTICS:
        (A) LENGTH: 1911 base pairs
        (B) TYPE: nucleotide
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
    (A) NAME/KEY: CDS
    (B) LOCATION:1..1911

(xi) SEQUENCE DESCRIPTION: SEQ ID NO: 3:

```
ATG GCA AGC TCT ACG ACT ACA CCG TTG TTA CCG CAC CAC CAT TTG CAG        48
Met Ala Ser Ser Thr Thr Thr Pro Leu Leu Pro His His His Leu Gln
        640             645             650

AAT CCT CAG CAG TTG GCT GGA AGT CCA GCT GCA CAC AGG TTG AGT CGT        96
Asn Pro Gln Gln Leu Ala Gly Ser Pro Ala Ala His Arg Leu Ser Arg
655             660             665

CCT ACT CTT TTG AGT GGT ATA TTG GTA AGT GTA CTG GTC ATC TGC GCA       144
Pro Thr Leu Leu Ser Gly Ile Leu Val Ser Val Leu Val Ile Cys Ala
670             675             680             685

TTG GTC GCA GTT ATA CAT AAT CAG TCT CAA CAG CCA TAC CAT GAT GGT       192
Leu Val Ala Val Ile His Asn Gln Ser Gln Gln Pro Tyr His Asp Gly
                690             695             700

GGT GCC AAG CCT AGC TCT AGC GCT GCC ACG ACT ACT TTT CCT ACA GCC       240
Gly Ala Lys Pro Ser Ser Ser Ala Ala Thr Thr Thr Phe Pro Thr Ala
        705             710             715

AGC CCT GAA GCA GGA TTG AAA AGA TTC CCT ATC GAA CTC AAG ACC AAC       288
Ser Pro Glu Ala Gly Leu Lys Arg Phe Pro Ile Glu Leu Lys Thr Asn
        720             725             730

GCA GAA GTC GAG TGG CAG AGA AGT GCA TAC CAC TTC CAG CCA GAT AAG       336
Ala Glu Val Glu Trp Gln Arg Ser Ala Tyr His Phe Gln Pro Asp Lys
        735             740             745

AAC TAT ATC TCA GAC CCA GAC GGG CCT ATG TAC CAT ATG GGT TGG TAC       384
Asn Tyr Ile Ser Asp Pro Asp Gly Pro Met Tyr His Met Gly Trp Tyr
750             755             760             765

CAC TTA TTC TAC CAA TAT AAT CCA GAG AGT GCA ATA TGG GGA AAT ATA       432
His Leu Phe Tyr Gln Tyr Asn Pro Glu Ser Ala Ile Trp Gly Asn Ile
                770             775             780

ACT TGG GGT CAT AGC GTT AGC AAG GAT ATG ATT AAT TGG TTT CAC TTG       480
Thr Trp Gly His Ser Val Ser Lys Asp Met Ile Asn Trp Phe His Leu
            785             790             795

CCA TTT GCG ATG GTC CCA GAT CAA TGG TAT GAT ATT GAG GGC GTT ATG       528
Pro Phe Ala Met Val Pro Asp Gln Trp Tyr Asp Ile Glu Gly Val Met
        800             805             810

ACT GGA AGC GCA ACT GTT TTG CCA GAC GGA CAG ATC ATT ATG TTG TAT       576
Thr Gly Ser Ala Thr Val Leu Pro Asp Gly Gln Ile Ile Met Leu Tyr
        815             820             825

ACC GGT AAT GCA TAC GAC TTG AGT CAG TTG CAG TGT CTC GCC TAT GCC       624
Thr Gly Asn Ala Tyr Asp Leu Ser Gln Leu Gln Cys Leu Ala Tyr Ala
830             835             840             845

GTT AAT AGC AGC GAC CCC TTG TTG CTC GAT TGG AAG AAG TAC GAG GGC       672
Val Asn Ser Ser Asp Pro Leu Leu Leu Asp Trp Lys Lys Tyr Glu Gly
                850             855             860

AAT CCG ATT CTC TTT CCG CCT CCT GGC GTC GGA TAT AAA GAT TTC AGA       720
Asn Pro Ile Leu Phe Pro Pro Pro Gly Val Gly Tyr Lys Asp Phe Arg
            865             870             875

GAT CCC AGT ACT CTC TGG CTC GGT CCA GAC GGA GAG TAC CGT ATG GTC       768
Asp Pro Ser Thr Leu Trp Leu Gly Pro Asp Gly Glu Tyr Arg Met Val
            880             885             890

ATG GGC AGC AAA CAC AAT GAA ACA ATC GGG TGC GCA CTC ATC TAT CAC       816
Met Gly Ser Lys His Asn Glu Thr Ile Gly Cys Ala Leu Ile Tyr His
        895             900             905

ACG ACA AAC TTC ACG CAC TTC GAG CTC AAG GAA GAA GTC TTA CAC GCT       864
Thr Thr Asn Phe Thr His Phe Glu Leu Lys Glu Glu Val Leu His Ala
910             915             920             925
```

-continued

```
GTT CCT CAC ACA GGA ATG TGG GAG TGC GTC GAC TTA TAT CCC GTC AGT           912
Val Pro His Thr Gly Met Trp Glu Cys Val Asp Leu Tyr Pro Val Ser
            930                 935                 940

ACT ACT CAT ACG AAT GGC TTG GAT ATG GTC GAC AAT GGT CCC AAC GTC           960
Thr Thr His Thr Asn Gly Leu Asp Met Val Asp Asn Gly Pro Asn Val
                945                 950                 955

AAA CAT GTC CTC AAG CAG TCC GGC GAC GAG GAC AGG CAC GAC TGG TAC          1008
Lys His Val Leu Lys Gln Ser Gly Asp Glu Asp Arg His Asp Trp Tyr
            960                 965                 970

GCT TTA GGT ACA TAT GAC GTC GTC AAC GAC AAA TGG TAT CCC GAC GAT          1056
Ala Leu Gly Thr Tyr Asp Val Val Asn Asp Lys Trp Tyr Pro Asp Asp
        975                 980                 985

CCC GAG AAC GAC GTC GGA ATT GGC CTT CGT TAC GAC TTC GGC AAG TTC          1104
Pro Glu Asn Asp Val Gly Ile Gly Leu Arg Tyr Asp Phe Gly Lys Phe
990                 995                 1000                1005

TAC GCC AGT AAA ACA TTC TAC GAT CAG CAC AAA AAA CGT CGT GTT TTA          1152
Tyr Ala Ser Lys Thr Phe Tyr Asp Gln His Lys Lys Arg Arg Val Leu
                1010                1015                1020

TGG GGA TAC GTC GGC GAG ACG GAC CCG CCC AAA TAC GAT GTC TAC AAA          1200
Trp Gly Tyr Val Gly Glu Thr Asp Pro Pro Lys Tyr Asp Val Tyr Lys
            1025                1030                1035

GGT TGG GCA AAT ATC CTC AAC ATA CCT CGC ACT ATT GTC CTC GAT ACG          1248
Gly Trp Ala Asn Ile Leu Asn Ile Pro Arg Thr Ile Val Leu Asp Thr
        1040                1045                1050

AAG ACA AAC ACG AAC CTC ATA CAG TGG CCT ATT GCC GAG GTG GAG AAT          1296
Lys Thr Asn Thr Asn Leu Ile Gln Trp Pro Ile Ala Glu Val Glu Asn
    1055                1060                1065

TTA CGT AGC AAC AAA TAC AAC GAG TTC AAG GAT GTG GAA TTG AAG CCT          1344
Leu Arg Ser Asn Lys Tyr Asn Glu Phe Lys Asp Val Glu Leu Lys Pro
1070                1075                1080                1085

GGA AGT TTG ATT CCG TTA GAA ATC GGT ACT GCT ACT CAA CTC GAC ATC          1392
Gly Ser Leu Ile Pro Leu Glu Ile Gly Thr Ala Thr Gln Leu Asp Ile
                1090                1095                1100

ACC GCT ACT TTT GAG GTC GAT CAG ACC ATG CTC GAG AGT ACC TTA GAA          1440
Thr Ala Thr Phe Glu Val Asp Gln Thr Met Leu Glu Ser Thr Leu Glu
            1105                1110                1115

GCG GAC GTA TTA TTT AAC TGT ACC ACA TCC GAG GGG AGC GCA GGT CGC          1488
Ala Asp Val Leu Phe Asn Cys Thr Thr Ser Glu Gly Ser Ala Gly Arg
        1120                1125                1130

GGA GTC CTT GGT CCA TTC GGA CTT GTC GTC TTA GCG GAC GCA GAA AGA          1536
Gly Val Leu Gly Pro Phe Gly Leu Val Val Leu Ala Asp Ala Glu Arg
    1135                1140                1145

AGC GAG CAG TTG CCC GTC TAT TTT TAC ATT GCC AAG GAC ACC GAC GGT          1584
Ser Glu Gln Leu Pro Val Tyr Phe Tyr Ile Ala Lys Asp Thr Asp Gly
1150                1155                1160                1165

TCC AGC AAG ACA TAC TTC TGC GCA GAT GAG TCC CGC AGC AGC AAC GAC          1632
Ser Ser Lys Thr Tyr Phe Cys Ala Asp Glu Ser Arg Ser Ser Asn Asp
                1170                1175                1180

GTC GAT ATC GGC AAG TGG GTC TAT GGT TCG TCA GTC CCA GTG TTG GAG          1680
Val Asp Ile Gly Lys Trp Val Tyr Gly Ser Ser Val Pro Val Leu Glu
            1185                1190                1195

GGA GAG AAA TTT AAC ATG CGC CTG CTT GTC GAC CAC AGC ATC GTC GAA          1728
Gly Glu Lys Phe Asn Met Arg Leu Leu Val Asp His Ser Ile Val Glu
        1200                1205                1210

GGC TTC GCT CAG GGT GGC CGT ACT GTC GTA ACC AGT CGT GTC TAC CCT          1776
Gly Phe Ala Gln Gly Gly Arg Thr Val Val Thr Ser Arg Val Tyr Pro
    1215                1220                1225

GCT AAA GCC ATA TAT GGG GCA GCC AAA CTC TTC CTC TTT AAT AAT GCC          1824
Ala Lys Ala Ile Tyr Gly Ala Ala Lys Leu Phe Leu Phe Asn Asn Ala
1230                1235                1240                1245
```

```
ACA GGC ATA TCA GTC AAA GCC AGC TTA AAA ATT TGG AAA ATG AAA GAG    1872
Thr Gly Ile Ser Val Lys Ala Ser Leu Lys Ile Trp Lys Met Lys Glu
            1250                1255                1260

GCT CAG TTG GAC CCG TTT CCA TTA AGC GGC TGG TCT AGC                1911
Ala Gln Leu Asp Pro Phe Pro Leu Ser Gly Trp Ser Ser
            1265                1270

(2) INFORMATION FOR SEQ ID NO: 4:

(i) SEQUENCE CHARACTERISTICS:
        (A) LENGTH: 637 amino acids
        (B) TYPE: amino acid
        (D) TOPOLOGY: linear (ii) MOLECULE TYPE: Protein (xi) SEQUENCE DESCRIPTION: SEQ ID NO: 4:

Met Ala Ser Ser Thr Thr Thr Pro Leu Leu Pro His His Leu Gln
 1               5                  10                  15

Asn Pro Gln Gln Leu Ala Gly Ser Pro Ala Ala His Arg Leu Ser Arg
            20                  25                  30

Pro Thr Leu Leu Ser Gly Ile Leu Val Ser Val Leu Val Ile Cys Ala
            35                  40                  45

Leu Val Ala Val Ile His Asn Gln Ser Gln Gln Pro Tyr His Asp Gly
 50                  55                  60

Gly Ala Lys Pro Ser Ser Ser Ala Ala Thr Thr Thr Phe Pro Thr Ala
 65                  70                  75                  80

Ser Pro Glu Ala Gly Leu Lys Arg Phe Pro Ile Glu Leu Lys Thr Asn
                85                  90                  95

Ala Glu Val Glu Trp Gln Arg Ser Ala Tyr His Phe Gln Pro Asp Lys
            100                 105                 110

Asn Tyr Ile Ser Asp Pro Asp Gly Pro Met Tyr His Met Gly Trp Tyr
            115                 120                 125

His Leu Phe Tyr Gln Tyr Asn Pro Glu Ser Ala Ile Trp Gly Asn Ile
            130                 135                 140

Thr Trp Gly His Ser Val Ser Lys Asp Met Ile Asn Trp Phe His Leu
145                 150                 155                 160

Pro Phe Ala Met Val Pro Asp Gln Trp Tyr Asp Ile Glu Gly Val Met
                165                 170                 175

Thr Gly Ser Ala Thr Val Leu Pro Asp Gly Gln Ile Ile Met Leu Tyr
            180                 185                 190

Thr Gly Asn Ala Tyr Asp Leu Ser Gln Leu Gln Cys Leu Ala Tyr Ala
            195                 200                 205

Val Asn Ser Ser Asp Pro Leu Leu Leu Asp Trp Lys Lys Tyr Glu Gly
210                 215                 220

Asn Pro Ile Leu Phe Pro Pro Gly Val Gly Tyr Lys Asp Phe Arg
225                 230                 235                 240

Asp Pro Ser Thr Leu Trp Leu Gly Pro Asp Gly Glu Tyr Arg Met Val
            245                 250                 255

Met Gly Ser Lys His Asn Glu Thr Ile Gly Cys Ala Leu Ile Tyr His
            260                 265                 270

Thr Thr Asn Phe Thr His Phe Glu Leu Lys Glu Val Leu His Ala
            275                 280                 285

Val Pro His Thr Gly Met Trp Glu Cys Val Asp Leu Tyr Pro Val Ser
            290                 295                 300

Thr Thr His Thr Asn Gly Leu Asp Met Val Asp Asn Gly Pro Asn Val
```

-continued

```
305                 310                 315                 320
Lys His Val Leu Lys Gln Ser Gly Asp Glu Asp Arg His Asp Trp Tyr
                325                 330                 335
Ala Leu Gly Thr Tyr Asp Val Val Asn Asp Lys Trp Tyr Pro Asp Asp
                340                 345                 350
Pro Glu Asn Asp Val Gly Ile Gly Leu Arg Tyr Asp Phe Gly Lys Phe
                355                 360                 365
Tyr Ala Ser Lys Thr Phe Tyr Asp Gln His Lys Lys Arg Arg Val Leu
                370                 375                 380
Trp Gly Tyr Val Gly Glu Thr Asp Pro Pro Lys Tyr Asp Val Tyr Lys
385                 390                 395                 400
Gly Trp Ala Asn Ile Leu Asn Ile Pro Arg Thr Ile Val Leu Asp Thr
                405                 410                 415
Lys Thr Asn Thr Asn Leu Ile Gln Trp Pro Ile Ala Glu Val Glu Asn
                420                 425                 430
Leu Arg Ser Asn Lys Tyr Asn Glu Phe Lys Asp Val Glu Leu Lys Pro
                435                 440                 445
Gly Ser Leu Ile Pro Leu Glu Ile Gly Thr Ala Thr Gln Leu Asp Ile
    450                 455                 460
Thr Ala Thr Phe Glu Val Asp Gln Thr Met Leu Glu Ser Thr Leu Glu
465                 470                 475                 480
Ala Asp Val Leu Phe Asn Cys Thr Thr Ser Glu Gly Ser Ala Gly Arg
                485                 490                 495
Gly Val Leu Gly Pro Phe Gly Leu Val Val Leu Ala Asp Ala Glu Arg
                500                 505                 510
Ser Glu Gln Leu Pro Val Tyr Phe Tyr Ile Ala Lys Asp Thr Asp Gly
    515                 520                 525
Ser Ser Lys Thr Tyr Phe Cys Ala Asp Glu Ser Arg Ser Ser Asn Asp
    530                 535                 540
Val Asp Ile Gly Lys Trp Val Tyr Gly Ser Ser Val Pro Val Leu Glu
545                 550                 555                 560
Gly Glu Lys Phe Asn Met Arg Leu Leu Val Asp His Ser Ile Val Glu
                565                 570                 575
Gly Phe Ala Gln Gly Gly Arg Thr Val Val Thr Ser Arg Val Tyr Pro
                580                 585                 590
Ala Lys Ala Ile Tyr Gly Ala Ala Lys Leu Phe Leu Phe Asn Asn Ala
    595                 600                 605
Thr Gly Ile Ser Val Lys Ala Ser Leu Lys Ile Trp Lys Met Lys Glu
    610                 615                 620
Ala Gln Leu Asp Pro Phe Pro Leu Ser Gly Trp Ser Ser
625                 630                 635
```